US009721180B2

(12) United States Patent
Prasad et al.

(10) Patent No.: US 9,721,180 B2
(45) Date of Patent: Aug. 1, 2017

(54) ESTIMATING RESPIRATORY PHASE FROM A VIDEO OF A SUBJECT

(71) Applicant: Xerox Corporation, Norwalk, CT (US)

(72) Inventors: Prathosh A. Prasad, Karnataka (IN);
Lalit Keshav Mestha, Fairport, NY (US); Himanshu J. Madhu, Mumbai Maharashtra (IN)

(73) Assignee: Xerox Corporation, Norwalk, CT (US)

(*) Notice: Subject to any disclaimer, the term of this patent is extended or adjusted under 35 U.S.C. 154(b) by 71 days.

(21) Appl. No.: 14/969,147

(22) Filed: Dec. 15, 2015

(65) Prior Publication Data

US 2017/0169307 A1 Jun. 15, 2017

(51) Int. Cl.
 *G06K 9/00* (2006.01)
 *G06K 9/46* (2006.01)
 *A61B 5/00* (2006.01)
 *A61B 5/08* (2006.01)
 *G06K 9/40* (2006.01)
 *A61B 5/113* (2006.01)
 *A61B 5/11* (2006.01)

(52) U.S. Cl.
 CPC .......... *G06K 9/4647* (2013.01); *A61B 5/0013* (2013.01); *A61B 5/0077* (2013.01); *A61B 5/08* (2013.01); *A61B 5/1128* (2013.01); *A61B 5/1135* (2013.01); *G06K 9/0053* (2013.01); *G06K 9/40* (2013.01); *G06K 9/4661* (2013.01); *A61B 2576/00* (2013.01); *G06K 2209/05* (2013.01)

(58) Field of Classification Search
None
See application file for complete search history.

(56) References Cited

PUBLICATIONS

Nakajima et al ("Evaluation of Body motion by optical flow analyis", 1997.*
Nakajima et al ("A method for measuring respiration and physical activity in bed by optical flow analysis", 1997.*
Beauchemin, S.S., et al., "The Computation of Optical Flow", ACM Computing Surveys, Sep. 1995, pp. 1-35, vol. 27, No. 3.
(Continued)

*Primary Examiner* — Avinash Yentrapati
(74) *Attorney, Agent, or Firm* — Philip E. Blair; Fleit Gibbons Gutman Bongini & Bianco P.L.

(57) ABSTRACT

A video is received of a region of a subject where a signal corresponding to respiratory function can be registered by a video device. Pixels in the region in each of the image frames are processed to identify a respiratory pattern with peak/valley pairs. A peak/valley pair of interest is selected. An array of optical flow vectors is determined between a window of groups of pixel locations in a reference image frame corresponding to a peak of the pair/valley pair and a window in each of a number of image frames corresponding to the respiratory signal between the peak and ending at a valley point. Optical flow vectors have a direction and a magnitude. A ratio is determined between upwardly pointing optical flow vectors and downwardly pointing optical flow vectors. Based on the ratio, a determination is made whether the respiration phase for that peak/valley pair is inspiration or expiration.

20 Claims, 8 Drawing Sheets

(56) References Cited

PUBLICATIONS

Chen, L., et al., "Algorithms to qualify respiratory data collected during the transport of trauma patients", Physiological Measurement, Jun. 2006, pp. 797-816, vol. 27, No. 9.
Baker, S., et al., "A Database and Evaluation Methodology for Optical Flow", International Journal of Computer Vision, Nov. 2010, pp. 1-31, vol. 92, No. 1.
Horn, B., et al., "Determining Optical Flow", 1981 Technical Symposium East, Nov. 1981, pp. 1-28.
Lucas, B., et al., "An Iterative Image Registration Technique with an Application to Stereo Vision", Proceedings of the Seventh International Joint Conference on Artificial Intelligence, Aug. 24-28, 1981, pp. 1-10.
Fleet, D., et al., "Optical Flow Estimation", appears in Mathematical Models in Computer Vision: The Handbook, Chapter 15, N. Paragios, et al., (editors), Springer, 2005, pp. 239-258.
Aires, K., et al., "Optical Flow Using Color Information: Preliminary Results", Proceedings of the 23rd ACM Symposium on Applied Computing, Mar. 16-20, 2008, pp. 1-5.
Barron, J.L., et al., "Performance of Optical Flow Techniques", International Journal of Computer Vision, Feb. 1994, vol. 12, No. 1, pp. 1-60.
U.S. Appl. No. 14/742,233, filed Jun. 17, 2015, Xerox.
U.S. Appl. No. 14/044,043, filed Oct. 2, 2013, Xerox.

\* cited by examiner

ESTIMATING RESPIRATORY PHASE FROM A VIDEO OF A SUBJECT

TECHNICAL FIELD

The present invention is directed to systems and methods for estimating respiratory phase from a video of a subject for respiratory function assessment.

BACKGROUND

Respiration is an important physiological activity that helps facilitate metabolism. Monitoring respiratory function is of great clinical significance. Continuous monitoring of respiratory events is also an important clinical requirement as it serves to detect potentially fatal events such as acute respiratory failure as well as pulmonary diseases. Existing methods to obtain patient data relating to respiratory function include devices such as spirometers, chest-belts, impedance pneumography which are contact-based devices. Such devices can be associated with discomfort and psychological dependence. In many diagnosis and therapeutic applications, it is desirable to know the precise intervals of both inspiration and expiration phases of respiration for reasons which include: assessment and intervention prediction for asthmatic and pulmonary patients where the analysis is to be carried out during the expiration phase; respiratory gated acquisition of radiological images where the X-ray device is triggered at a pre-defined phase of the respiratory cycle; and respiratory gated therapeutic shock delivery systems where acoustic shocks are delivered in-phase with the respiratory cycles.

Accordingly, what is needed in this art is a system and method for estimating respiratory phase from a video of a subject.

BRIEF SUMMARY

What is disclosed is a system and method for estimating respiratory phase from a video of a subject for respiratory function assessment. One embodiment of the present method involves performing the following. First, a video of a subject is received. The video comprises image frames of a region of the subject where a signal corresponding to the subject's respiratory function can be registered by at least one imaging channel of a video imaging device used to capture the video. Next, the pixels in the region in each of the image frames are processed to identify a respiratory pattern which comprises a respiratory signal with temporally successive peak/valley pairs. A peak/valley pair of interest is selected for which respiratory phase is desired to be determined. An array of optical flow vectors is determined between a window of pixel locations in a reference image frame which corresponds to the peak of the selected pair/valley pair and a similarly sized window in each of a pre-defined number of image frames which correspond to the respiratory signal occurring between the peak and ending at the valley point. The optical flow vectors have a direction corresponding to motion caused by temporal variations in intensity and a magnitude corresponding to an amount of the variation. A ratio is determined between optical flow vectors having a upwardly pointing direction to optical flow vectors having a downwardly pointing direction. Based on the ratio, a determination is made whether the respiration phase for the selected peak/valley pair is inspiration or expiration. Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for estimating respiratory phase defined as intervals of inspiration and expiration from a video of a subject for respiratory function assessment.

It should be understood that one of skilled in this art would readily understand various aspects of image processing, and methods for generating time-series signals from pixels obtained from batches of image frames in a video. One skilled in this art would also be readily familiar with optical flow techniques and algorithms.

Non-Limiting Definitions

Figure 1:
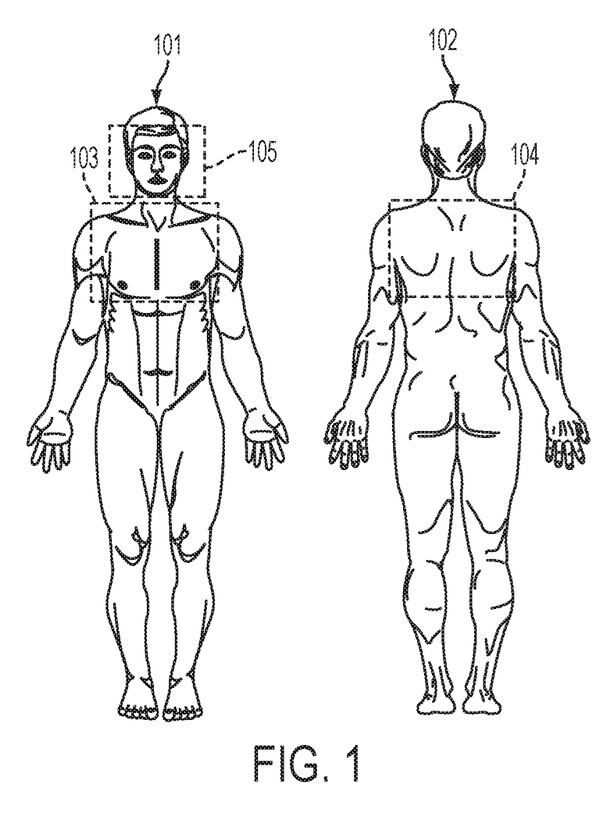
FIG. 1 shows an anterior view of an adult human as well as a posterior view.

A "subject" refers to a living being. Although the term "person" or "patient" may be used throughout this disclosure, it should be appreciated that the subject may be something other than a human such as, for example, a primate. Therefore, the use of such terms is not to be viewed as limiting the scope of the appended claims strictly to human beings with a respiratory function. FIG. 1 shows an anterior (frontal) view 101 of an adult human as well as a posterior (rear) view 102. The subject in the video can be any distance away from the medical practitioner with the video of the subject being communicated to a workstation over a wired or wireless network.

"Respiratory function" is a process of inspiration of air into the lungs (inhalation) and expiration of air out of the lungs (exhalation) followed by a brief post-expiratory pause. The expansion and contraction of the lungs and chest walls induces a movement in the subject's body which is captured in a video of the subject.

A "video", as is generally understood, refers to a plurality of time-sequential image frames captured of a region of a subject where a signal corresponding to respiratory function can be registered by at least one imaging channel of the video imaging device used to capture that video. The video may also contain other components such as, audio, time, date, reference signals, frame information, and the like.

Figure 2:
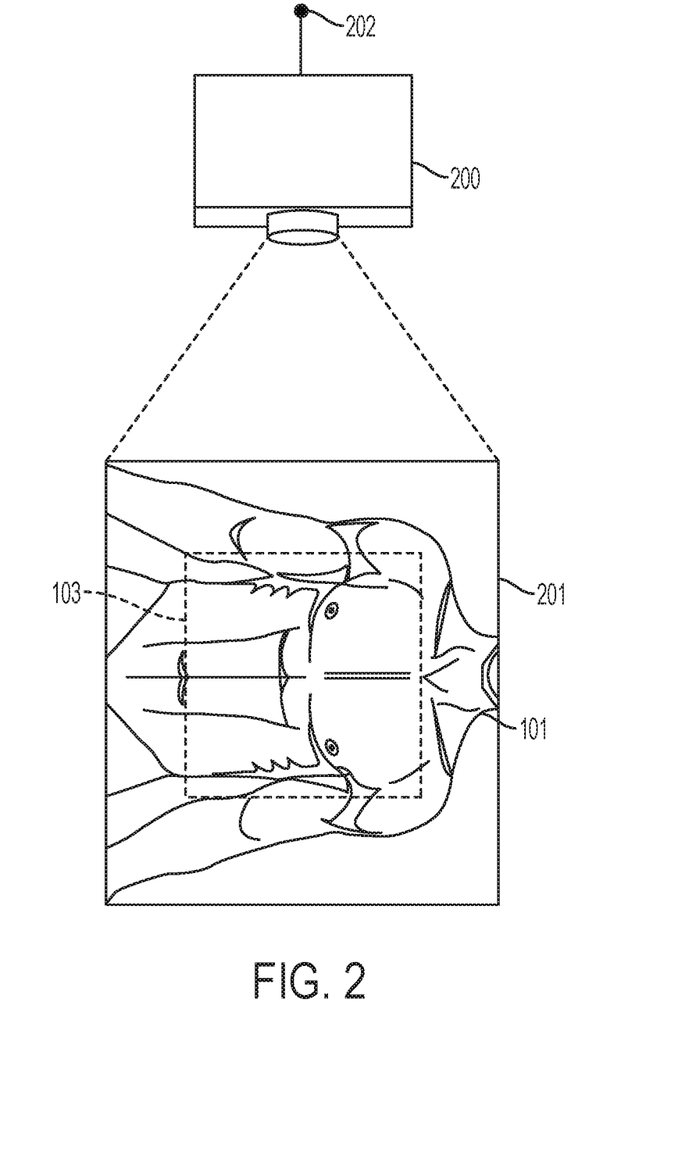
FIG. 2 shows an example video imaging device capturing image frames of a region of interest of the subject of FIG. 1.

A "video imaging device" refers to a video camera such as, for example, a color video camera, a monochrome video camera, an infrared video camera, a multispectral video imaging device, a hyperspectral video camera, and a hybrid device comprising any combination hereof. FIG. 2 shows an example video imaging device 200 capturing image frames (individually at 201) of a region 103 of the subject of FIG. 1. The video imaging device is shown having a communication element 202, shown as an antenna, which effectuates communication with a remote device such as a workstation over a wireless network where the image frames are received for processing in accordance with the methods disclosed herein. The video imaging device may incorporate memory, a storage device, and a video analysis module comprising one or more microprocessors for executing machine readable program instructions for processing the video. Such a video analysis module may comprise, in whole or in part, a software application working alone or in conjunction with one or more hardware resources. Software applications may be executed by processors on different hardware platforms or emulated in a virtual environment and may leverage off-the-shelf software.

"Receiving a video" is intended to be widely construed and includes retrieving, capturing, acquiring, or otherwise obtaining video image frames. The video can be received or retrieved from a remote device over a network, or from a media such as a CDROM or DVD. Video may be downloaded from a web-based system or application which makes video available for processing in accordance with the methods disclosed herein. Video can also be received from an application such as those which are available for handheld cellular devices and processed on the cellphone or other handheld computing device such as an iPad or Tablet-PC. The video can be received directly from a memory or storage device of the video imaging device used to capture that video.

A "region of the subject" refers to at least a partial view of the subject as seen through the aperture of the video imaging device where a respiratory signal corresponding to respiratory function can be registered by at least one imaging channel of the video imaging device used to capture that video. Regions which move during respiration include the thoracic region such as the chest and abdomen, and facial regions such as nostrils, lips, and cheeks. In FIG. 1, regions 103 and 104 outline the subject's anterior thoracic region and posterior thoracic region, respectively. Signals associated with respiratory function can also be sensed by the video imaging device in a facial region 105. The region may be an area of exposed skin or an area covered by a sheet or an article of clothing. Regions can be identified in image frames of the video by a user input or selection. For example, an operator or technician may use a mouse or a touchscreen display to draw a rubber-band box around one or more areas of the video of the subject displayed on a monitor thereby defining a region of pixels to be processed to obtain a respiratory pattern for the subject.

Figure 3:
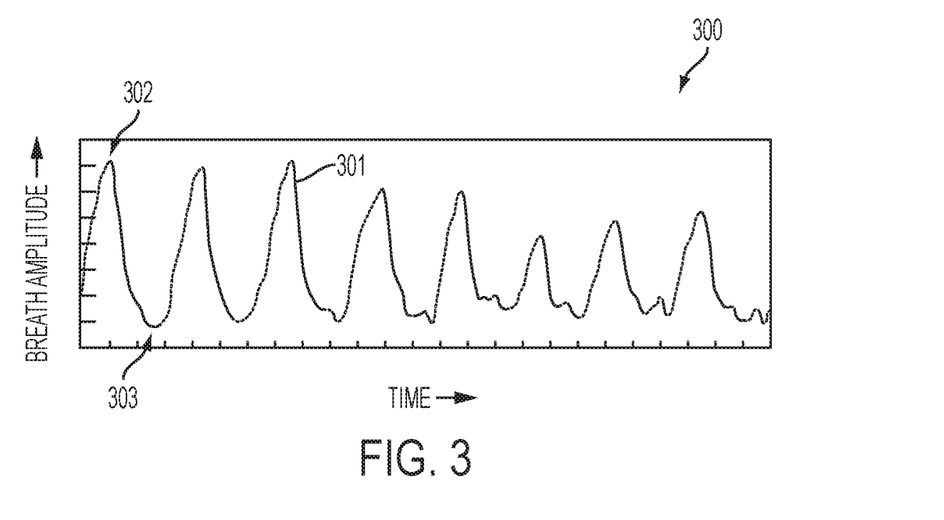
FIG. 3 shows an example breathing pattern identified for the subject in FIG. 2 which is associated with normal breathing.

A "respiratory pattern" refers to a pattern of breathing. Respiratory patterns include: Eupnea, Bradypnea, Tachypnea, Hypopnea, Apnea, Kussmaul, Cheyne-Stokes, Biot's, Ataxic, Apneustic, Agonal, and Thoracoabdominal, as are understood in the medical arts. Methods for determining a respiratory pattern from a video are disclosed in: "Determining A Respiratory Pattern From A Video Of A Subject", U.S. patent application Ser. No. 14/742,233, by Prathosh A. Prasad et al., and "Breathing Pattern Identification For Respiratory Function Assessment", U.S. patent application Ser. No. 14/044,043, by Lalit K. Mestha et al. FIG. 3 shows an example breathing pattern 300. The respiratory pattern comprises a respiratory signal 301 which contains temporally successive peak/valley pairs.

A "peak/valley pair" refers to a peak in the respiratory signal and a valley point, as is widely understood in the signal processing arts. A first peak/valley pair is shown at 302 and 303, respectively. Methods for identifying or otherwise detecting a peak/valley pair in a signal include a manual selection by a user and the use of any of a wide array of automatic peak detection methods that are well established. In accordance with the methods disclosed herein, a peak/valley pair is processed along with corresponding image frames of the video of the subject to generate optical flow vectors.

Introduction to Optical Flow

The concept of optical flow was introduced by James J. Gibson in the 1940's to help understand and describe the role visual stimulus plays in the perception of movement in the mind of an observer. Gibson postulated that sequences of ordered images allow the estimation of motion as either instantaneous image velocities or discrete image displacements. A tutorial is disclosed in: "*Handbook of Mathematical Models in Computer Vision*", Paragios et al., Springer (2006), ISBN-13: 978-0387263717, [See, chapter entitled: "*Optical Flow Estimation*", by David J. Fleet and Yair Weiss, which provides an introduction to gradient based optical flow analysis].

Optical flow analysis tries to calculate motion between two image frames which are taken at times t and t+Δt at various pixel locations common to both images or at locations of groups of pixels common to both images. These methods are often referred to as differential methods since they are based on local Taylor series approximations, i.e., they use partial derivatives with respect to the spatial and temporal coordinates.

Generally, for a 2D+t dimensional case (3D or n-D cases are similar) values in the image at location (x,y,t) having intensity I(x,y,t) will have moved an amount given by Δx, Δy and Δt between two image frames, such that:

$$I(x,y,t) = I(x+\Delta x, y+\Delta y, t+\Delta t) \tag{1}$$

Assuming the movement is small, the respective Taylor series can be given as:

$$I(x+\Delta x, y+\Delta y, t+\Delta t) = I(x,y,t) + \frac{\partial I}{\partial x}\Delta x + \frac{\partial I}{\partial y}\Delta y + \frac{\partial I}{\partial t}\Delta t + \ldots \tag{2}$$

From Eqs. (1) and (2), it follows that:

$$\frac{\partial I}{\partial x}\Delta x + \frac{\partial I}{\partial y}\Delta y + \frac{\partial I}{\partial t}\Delta t = 0 \tag{3}$$

which results in:

$$\frac{\partial I}{\partial x}V_x + \frac{\partial I}{\partial y}V_y + \frac{\partial I}{\partial t}V_t = 0 \tag{4}$$

where $V_x$, $V_y$ are the x and y components of the velocity or optical flow of I(x,y,t) and $$\frac{\partial I}{\partial x}, \frac{\partial I}{\partial y}$$

and $$\frac{\partial I}{\partial t}$$

are the derivatives of the image at (x,y,t) in the corresponding directions.

Given the above, $I_x$, $I_y$ and $I_t$ can be written for the derivatives. Thus:

$$I_x V_x + I_y V_y = -I_t \quad (5)$$

Alternatively, $$\nabla I^T \cdot \vec{V} = -I_t \quad (6)$$

Eq. (6) has two unknowns. This is known as the aperture problem of optical flow algorithms. To find the optical flow, another set of equations is needed, given by some additional constraint. All optical flow methods introduce additional conditions for estimating the actual flow. A result of having performed optical flow analysis on an image or a window within an image produces an array of optical flow vectors.

Figure 4:
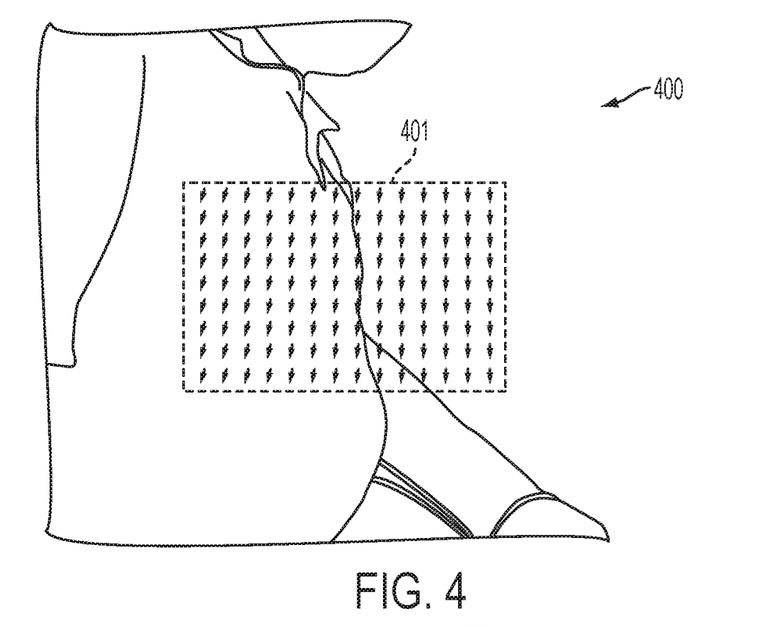
FIGS. 4 and 5 are images with optical flow vectors having been computed thereon.
Figure 5:
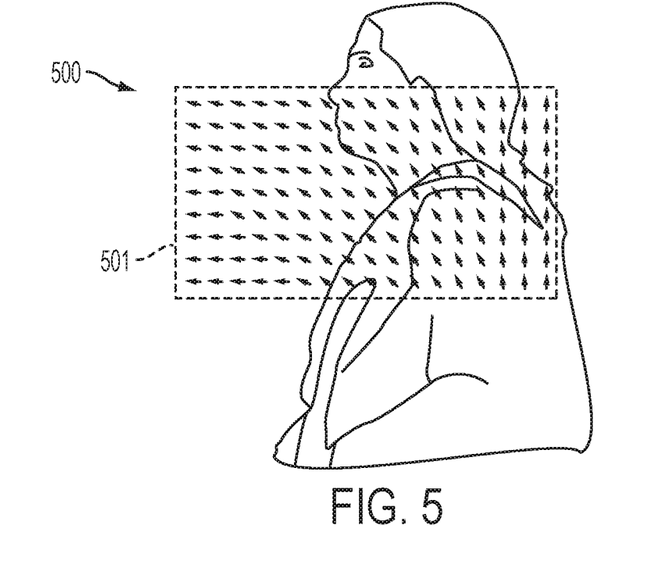

An "optical flow vector" is a vector, as is generally understood, having a direction and a magnitude. In general, optical flow refers to a pattern of apparent motion of an object in a scene caused by the relative motion between an observer (an eye or a camera) and the object. Example images 400 and 500 with optical flow vectors generated therefrom are shown in FIGS. 4 and 5, respectively. The optical flow vectors are shown having been generated for pixels within windows 401 and 501, respectively.

Methods for optical flow analysis include: the Lucas-Kanade Method as disclosed in: "*An Iterative Image Registration Technique with an Application to Stereo Vision*", Bruce D. Lucas and Takeo Kanade, Proc. of Imaging Understanding Workshop, pp. 121-130, (1981), the Horn-Schunck Method as disclosed in: "*Determining Optical Flow*", Berthold K. P. Horn and Brian G. Schunck, Vol 17, pp 185-203, Artificial Intelligence, (1981), and the Black-Jepson Method as disclosed in: "*Computation of Optical Flow*", S. S. Beauchemin, J. L. Barron, ACM Computing Surveys, Vol. 27, No. 3, (September 1995). It should also be appreciated that discrete optimization methods can also be employed.

Other methods are discussed in: "*A Database and Evaluation Methodology for Optical Flow*", Simon Baker, Daniel Scharstein, J. P. Lewis, Stefan Roth, Michael J. Black, Richard Szeliski, International Journal of Computer Vision, Vol. 92, pp. 1-31 (2011). It should be understood that the optical flow methods listed herein are representative and not exhaustive. Therefore the scope of the appended claims should not be limited to only these techniques.

"Respiratory phase", as used herein, refers to either the inspiration phase of the respiratory signal (i.e., when air is being drawn into the lungs) or the expiration phase of the respiratory signal (i.e., when air is being expelled from the lungs) for a given peak/valley pair. Respiratory phase is determined by a ratio of optical flow vectors.

A "ratio of optical flow vectors" is determined between the number of upwardly pointing optical flow vectors to the number of downwardly pointing optical flow vectors. Based on the ratio, the respiration phase for the selected peak/valley pair is determined to be either inspiration or expiration. In one embodiment, if the ratio is above 1 then it is determined that the respiration phase of the selected peak/valley pair is at inspiration, and at expiration otherwise.

It should be appreciated that the method steps of: "receiving", "isolating", "extracting", "processing", "selecting", "generating", "determining", "performing", "filtering", "locating", "computing", and the like, include the application of any of a variety of signal processing techniques as are known in the signal processing wherein, in response to said ratio being higher than one, determining that the respiration phase of the selected peak/valley pair is inspiration, and expiration otherwise arts, as well as a variety of mathematical operations according to any specific context or for any specific purpose. It should be appreciated that such steps may be facilitated or otherwise effectuated by a microprocessor executing machine readable program instructions such that an intended functionality can be effectively performed.

Example Flow Diagram

Figure 6:
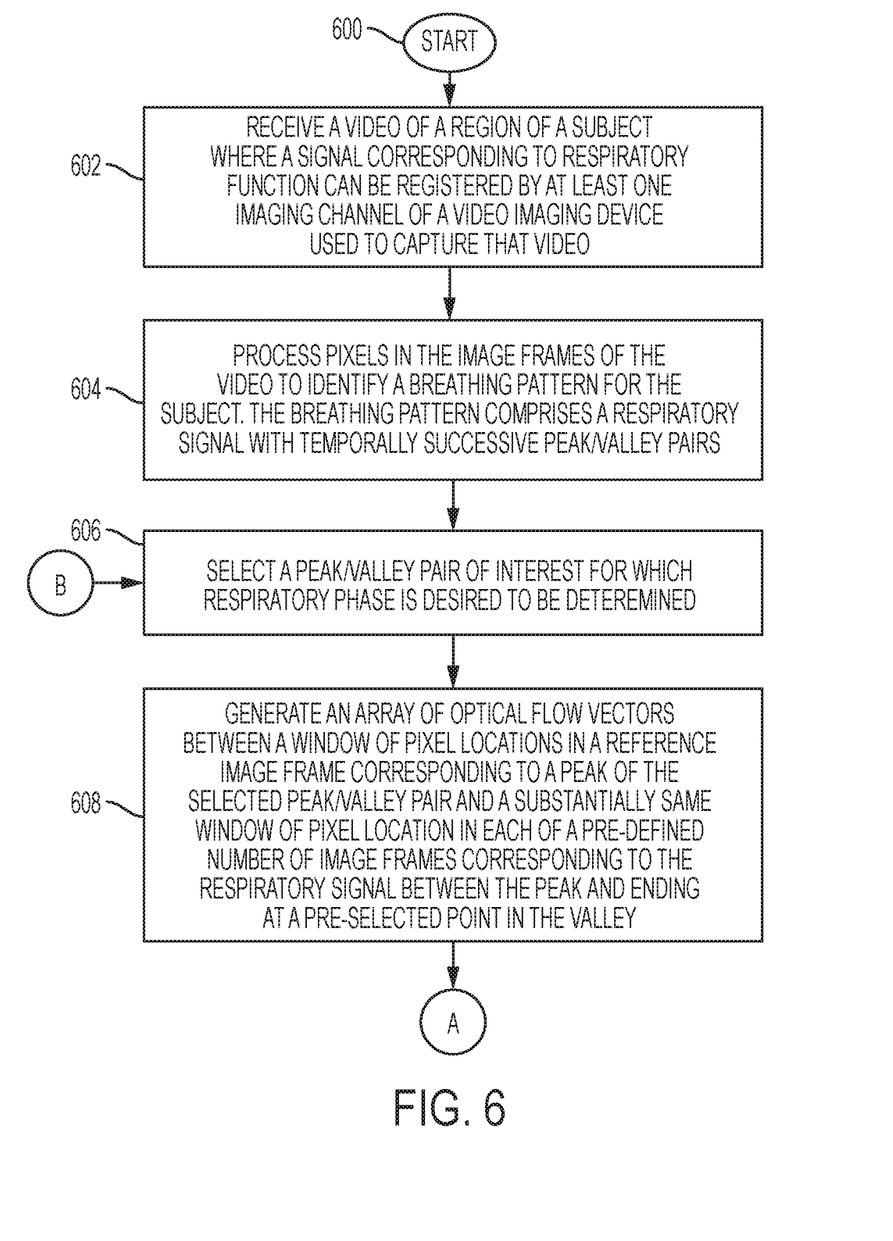
FIG. 6 is a flow diagram which illustrates one embodiment of the present method for respiratory phase estimation from a video of a subject.

Reference is now being made to the flow diagram of FIG. 6 which illustrates one embodiment of the present method for respiratory phase estimation from a video of a subject. Flow processing begins at step 600 and immediately proceeds to step 602.

At step 602, receive a video of a region of a subject where a signal corresponding to respiratory function can be registered by at least one imaging channel of a video imaging device used to capture that video.

At step 604, process pixels in the image frames to identify a respiratory pattern for the subject. The respiratory pattern comprises a respiratory signal with temporally successive peak/valley pairs. An example respiratory signal is shown in FIG. 3.

At step 606, select a peak/valley pair of interest for which respiratory phase is desired to be determined. One exampled selected peak/valley pair is shown at 302 and 303 of FIG. 3.

At step 608, generate an array of optical flow vectors between a window of pixel locations in a reference image frame corresponding to a peak of the selected pair/valley pair and a substantially same window of pixel locations in each of a pre-defined number of image frames corresponding to the respiratory signal between the peak and ending at a pre-selected point in the valley. Images with optical flow vectors are shown in FIGS. 4 and 5. As shown, the optical flow vectors have a direction corresponding to motion caused by temporal variations in intensity and a magnitude corresponding to an amount of the variation.

Figure 7:
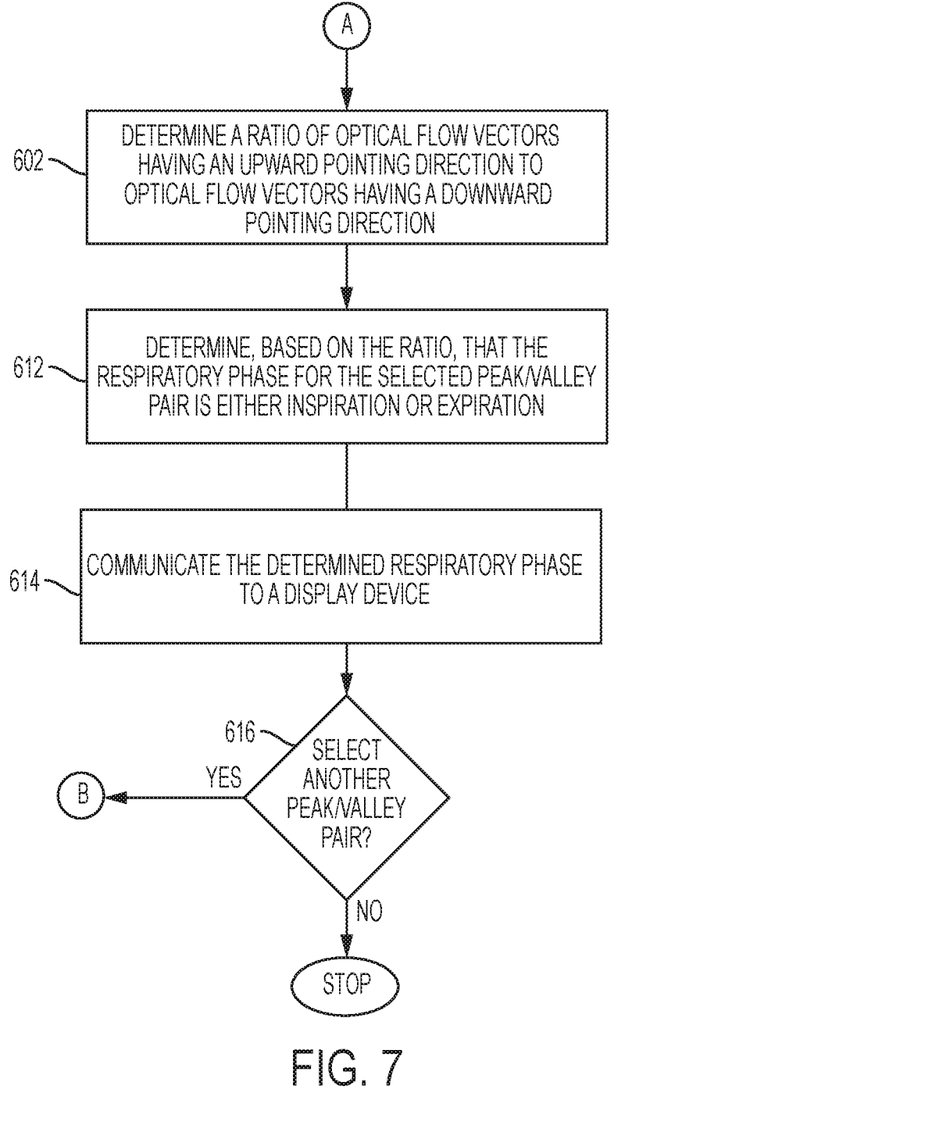
FIG. 7 is a continuation of the flow diagram of FIG. 6 with flow processing continuing with respect to node A.

Reference is now being made to the flow diagram of FIG. 7, which is a continuation of the flow diagram of FIG. 6 with flow processing continuing with respect to node A.

At step 610, determine a ratio of optical flow vectors having an upward pointing direction to optical flow vectors having a downward pointing direction. Such a determination can be made either manually or automatically using, for example, a processor executing machine readable programming instructions to perform this.

At step 612, determine, based on the ratio, that the respiration phase for the selected peak/valley pair is one of: inspiration and expiration.

At step 614, communicate the determined respiration phase to a display device. The result of the determination based on the ratio can also be stored to the storage device such as a memory or a hard drive.

At step 616, a determination is made whether to select another peak/valley pair for respiration phase determination. If so, then processing repeats with respect to node B wherein, at step 606, a next peak/valley pair of interest is selected for processing. Processing repeats in a similar manner until no more peak/valley pairs are desired to be selected. Thereafter, in this embodiment, further processing stops.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Block Diagram of Video Processing System

Figure 8:
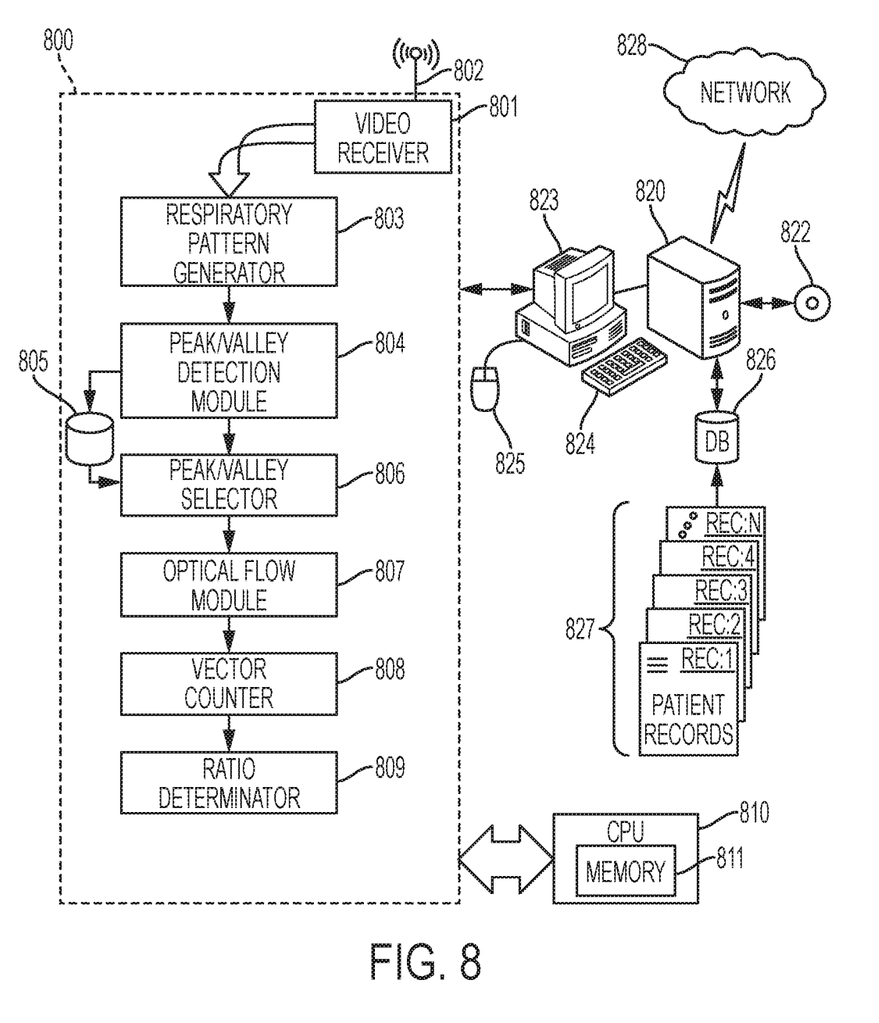
FIG. 8 shows a functional block diagram of one example video processing system 800 for processing a video in accordance with the embodiments described with respect to the flow diagrams of FIGS. 6-7.

Reference is now being made to FIG. 8 which shows a block diagram of one example video processing system 800 for processing a video in accordance with the embodiments described with respect to the flow diagrams of FIGS. 6-7.

Video Receiver 801 wirelessly receives the video via antenna 802 having been transmitted thereto from the video imaging device 200 of FIG. 2 using communication element 202. Respiratory Pattern Generator 803 generates a respiratory pattern for the subject from the received video of the subject. Peak/Valley Detector receives the generated respiratory pattern and proceeds to detect peak/valley pairs in the respiratory signal. Results are communicated to storage device 805. Peak/Valley Selector Module 806 retrieves the stored peak/valley pairs and selects a peak/valley pair of interest for which respiratory phase is desired to be determined. Peak/valley pairs of interest may also be selected by a user using, for instance, the keyboard, mouse and display device of the workstation 820. Optical Flow Module 807 receives the selected peak/valley pair of interest and proceeds to generate optical flow vectors for image frames in the video corresponding to the selected peak/valley pair, in a manner as disclosed herein. Vector Counter 808 receives the optical flow vectors for the processed images frames and proceeds to count the number of optical flow vectors having an upwardly pointing direction and the number of optical flow vectors having a downwardly pointing direction. Ratio Determinator 809 receives the count of upwardly and downwardly pointing optical vectors and proceeds to determine whether the respiratory phase for the selected peak/valley pair is one of inspiration or expiration.

Central Processing Unit 810 retrieves machine readable program instructions from a memory 811 and is provided to facilitate the functionality of any of the modules and processing units of the system 800. CPU 810, operating alone or in conjunction with other processors, may be configured to assist or otherwise perform the functionality of any of the modules or processing units of the system 800, as well as facilitating communication between the video processing system 800 and the workstation 820.

Workstation 820 is shown generally comprising a computer case which houses various components such as a motherboard with a microprocessor and memory, a network card, a video card, a hard drive capable of reading/writing to machine readable media 822 such as a floppy disk, optical disk, CD-ROM, DVD, magnetic tape, and the like, and other software and hardware as is needed to perform the functionality of a computer workstation. The workstation includes a display device 823, such as a CRT, LCD, or touchscreen display, for displaying information, image frames, vector magnitudes, vector intensities, optical flow vectors, computed values, patient medical information, and the like, which are produced or are otherwise generated by any of the modules or processing units of the video processing system 800. A user can view any such information and make a selection from various menu options displayed thereon. Keyboard 824 and mouse 825 effectuate a user input or selection. It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for performing various aspects of the methods disclosed herein.

A user may use the workstation to identify a set of image frames of interest, set various parameters, and other facilitate the functionality of any of the modules or processing units of the video processing system 800. A user or technician may utilize the workstation to select peak/valley pairs of interest, modify, add or delete vectors or move the window around or re-size the window as is deemed appropriate. The user may adjust various parameters being utilized or dynamically adjust in real-time, system or settings of any device used to capture the video images.

User inputs and selections may be stored/retrieved to/from any of the storage devices 805, 822 and 826. Default settings and initial parameters can be retrieved from any of the storage devices. The system 800 may communicate to one or more remote devices over network 828, utilizing a wired, wireless, or cellular communication protocol. Although shown as a desktop computer, it should be appreciated that the workstation can be a laptop, mainframe, tablet, notebook, smartphone, or a special purpose computer such as an ASIC, or the like. The embodiment of the workstation is illustrative and may include other functionality known in the arts.

The workstation implements a database in storage device 826 wherein records are stored, manipulated, and retrieved in response to a query. Such records, in various embodiments, take the form of patient medical history stored in association with information identifying the patient (collectively at 827). It should be appreciated that database 826 may be the same as storage device 805 or, if separate devices, may contain some or all of the information contained in either device. Although the database is shown as an external device, the database may be internal to the workstation mounted, for example, on a hard drive.

Any of the components of the workstation may be placed in communication with any of the modules of system 800 or any devices placed in communication therewith. Moreover, any of the modules of system 800 can be placed in communication with storage device 826 and/or computer readable media 822 and may store/retrieve therefrom data, variables, records, parameters, functions, and/or machine readable/executable program instructions, as needed to perform their intended functionality. Further, any of the modules or processing units of the system 800 may be placed in communication with one or more remote devices over network 828. It should be appreciated that some or all of the functionality performed by any of the modules or processing units of system 800 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

Performance Results

Figure 9:
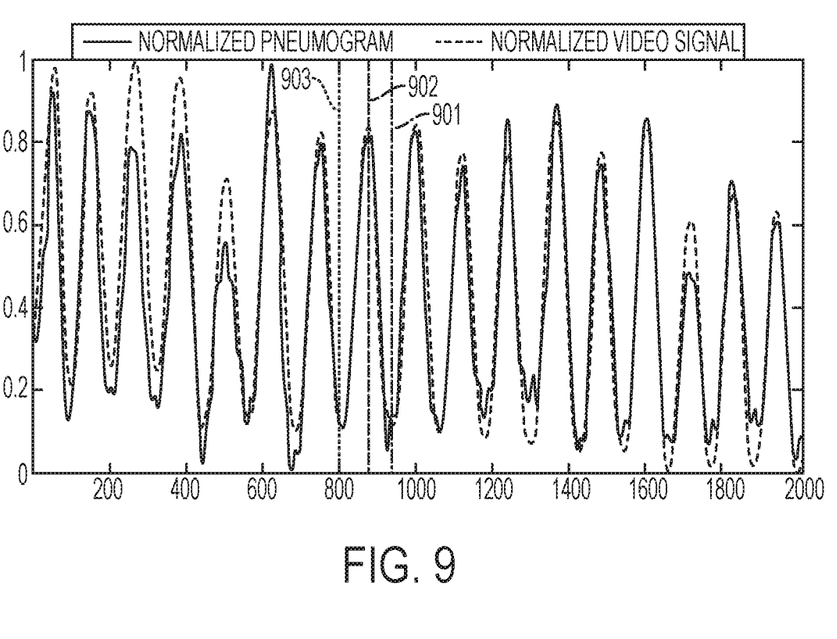
FIG. 9 shows a sample overlay between the pneumographic signal and the signal generated using video and phase compensation.

Data was collected from five human subjects who were asked to breathe in a tidal breathing pattern while wearing an impedance pneumographic device which would generate the ground truth. Simultaneously, video was captured of the subjects. Once the data was collected, it was processed using the methods hereof to generate their respective respiratory patterns. For each subject, a few peak/valley pairs were identified randomly. The Lucas-Kanade Algorithm was used for differential optical flow computation. The evaluation metric was the percentage of cycles correctly determined by the present method as compared to the ground truth. The results are shown in FIG. 9 which is a sample overlay between the pneumographic signal and the signal generated using video and phase compensation. The expiration cycle is the interval between lines 1001 and 1002 and the inspiration cycle is the interval between lines 1003 and 1002. FIG. 9 demonstrates that the present method accurately identifies respiratory phases from a video of the subject.

Various Embodiments

The teachings hereof can be implemented in hardware or software using any known or later developed systems, structures, devices, and/or software by those skilled in the applicable arts without undue experimentation from the functional description provided herein with a general knowledge of the relevant arts. One or more aspects of the methods described herein are intended to be incorporated in an article of manufacture. The article of manufacture may be shipped, sold, leased, or otherwise provided separately either alone or as part of a product suite or a service.

The above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are hereby incorporated in their entirety by reference being made thereto.

What is claimed is:

1. A computer implemented method for respiratory phase estimation from a video of a subject for respiratory function assessment, the method comprising:

receiving a video of a subject, said video comprising image frames of a region of said subject where a signal corresponding to said subject's respiratory function can be registered by at least one imaging channel of a video imaging device used to capture said video;

processing pixels in said image frames to identify a respiratory pattern for said subject, said respiratory pattern comprising a respiratory signal with temporally successive peak/valley pairs;

selecting a peak/valley pair of interest for which respiratory phase is desired to be determined;

generating an array of optical flow vectors between a window of pixel locations in a reference image frame corresponding to a peak of said selected peak/valley pair and a substantially same window of pixel locations in each of a pre-defined number of image frames corresponding to said respiratory signal between said peak and ending at a preselected point in said valley, said optical flow vectors having a direction corresponding to motion caused by temporal variations in intensity and a magnitude corresponding to an amount of said variation;

determining a ratio of optical flow vectors having an upward pointing direction to optical flow vectors having a downward pointing direction; and determining, based on said ratio, that said respiration phase for said selected peak/valley pair is one of: inspiration and expiration.

2. The method of claim 1, wherein said video imaging device is any of: a color video camera, an infrared video camera, a monochrome video camera, a multispectral video imaging device, a hyperspectral video camera, and a hybrid device comprising any combination hereof.

3. The method of claim 1, wherein, in advance of determining said ratio, pre-selecting only those optical flow vectors which have a magnitude that exceeds a pre-defined threshold.

4. The method of claim 1, wherein identifying said peak/valley pairs comprises:

filtering said respiratory signal with a moving average filter to obtain a smoothed signal;

computing a derivative of said smoothed signal; and locating positive and negative zero-crossings in said derivative corresponding to peaks and valleys.

5. The method of claim 1, wherein identifying said peak/valley pairs is performed by one of: a manual selection method and an automatic peak detection method.

6. The method of claim 1, wherein said window has a size that is at least equal to half a size of an image frame.

7. The method of claim 1, wherein said optical flow vectors are generated between a pairs of frames with a given frame corresponding to a peak as said reference frame.

8. The method of claim 1, wherein generating said optical flow vectors utilizes a method comprising any of: a Lucas-Kanade, a Horn-Schunck, and a Black-Jepson method.

9. The method of claim 8, further comprising aggregating said resolved optical flow vectors using one of: a maximum vote, and a mean value metric.

10. The method of claim 1, wherein, in response to said ratio being higher than one, determining that said respiration phase of said selected peak/valley pair is inspiration, and expiration otherwise.

11. A system for respiratory phase estimation from a video of a subject for respiratory function assessment, the system comprising:

a processor in communication with a memory, the processor executing machine readable instructions for performing the steps of:

receiving a video of a subject, said video comprising image frames of a region of said subject where a signal corresponding to said subject's respiratory function can be registered by at least one imaging channel of a video imaging device used to capture said video;

processing pixels in said image frames to identify a respiratory pattern for said subject, said respiratory pattern comprising a respiratory signal with temporally successive peak/valley pairs;

selecting a peak/valley pair of interest for which respiratory phase is desired to be determined;

generating an array of optical flow vectors between a window of pixel locations in a reference image frame corresponding to a peak of said selected peak/valley pair and a substantially same window of pixel locations in each of a pre-defined number of image frames corresponding to said respiratory signal between said peak and ending at a pre-selected point in said valley, said optical flow vectors having a direction corresponding to motion caused by temporal variations in intensity and a magnitude corresponding to an amount of said variation;

determining a ratio of optical flow vectors having an upward pointing direction to optical flow vectors having a downward pointing direction;

determining, based on said ratio, that said respiration phase for said selected peak/valley pair is one of: inspiration and expiration; and storing a result of said determination based on said ratio to said memory.

12. The system of claim 10, wherein said video imaging device is any of: a color video camera, an infrared video camera, a monochrome video camera, a multispectral video imaging device, a hyperspectral video camera, and a hybrid device comprising any combination hereof.

13. The system of claim 10, wherein, in advance of determining said ratio, pre-selecting only those optical flow vectors which have a magnitude that exceeds a pre-defined threshold.

14. The system of claim 10, wherein identifying said peak/valley pairs comprises:

filtering said respiratory signal with a moving average filter to obtain a smoothed signal;

computing a derivative of said smoothed signal; and locating positive and negative zero-crossings in said derivative corresponding to peaks and valleys.

15. The system of claim 10, wherein identifying said peak/valley pairs is performed by one of: a manual selection method and an automatic peak detection method.

16. The system of claim 10, wherein said window has a size that is at least equal to half a size of an image frame.

17. The system of claim 10, wherein said optical flow vectors are generated between a pairs of frames with a given frame corresponding to a peak as said reference frame.

18. The system of claim 10, wherein generating said optical flow vectors utilizes a method comprising any of: a Lucas-Kanade, a Horn-Schunck, and a Black-Jepson method.

19. The system of claim 18, further comprising aggregating said resolved optical flow vectors using one of: a maximum vote, and a mean value metric.

20. The system of claim 10, wherein, in response to said ratio being higher than one, determining that said respiration phase of said selected peak/valley pair is inspiration, and expiration otherwise.

* * * * *